United States Patent
Grandgeorge et al.

(10) Patent No.: US 6,372,510 B1
(45) Date of Patent: Apr. 16, 2002

(54) METHOD FOR REMOVING UNCONVENTIONAL TRANSMISSIBLE AGENTS FROM A PROTEIN SOLUTION

(75) Inventors: Michel Grandgeorge, Vaugneray; René Labatut, Saint-Genis-Laval; Jean-Marc Rouzioux, Tassin-la-Demi-Lune; Jean-Louis Tayot, La-Tour-de-Salvagny; Jean-Luc Veron, Ostwald, all of (FR)

(73) Assignee: Pasteur Merieux Serum et Vaccins, Lyons (FR)

( * ) Notice: Subject to any disclaimer, the term of this patent is extended or adjusted under 35 U.S.C. 154(b) by 0 days.

(21) Appl. No.: 09/142,745

(22) PCT Filed: Mar. 14, 1997

(86) PCT No.: PCT/FR97/00465

§ 371 Date: Nov. 10, 1998

§ 102(e) Date: Nov. 10, 1998

(87) PCT Pub. No.: WO97/34642

PCT Pub. Date: Sep. 25, 1997

(30) Foreign Application Priority Data

Mar. 15, 1996 (FR) .............................................. 96 03549
Jul. 9, 1996 (FR) .............................................. 96 08548

(51) Int. Cl.⁷ .......................... G01N 30/02; G01N 33/00
(52) U.S. Cl. ........................... 436/161; 436/86; 436/88; 530/412; 530/413; 530/362; 530/363; 530/364
(58) Field of Search .......................... 436/161, 86, 88; 530/412, 413, 416, 362, 363, 364

(56) References Cited

U.S. PATENT DOCUMENTS

| | | | | |
|---|---|---|---|---|
| 5,500,374 A | * | 3/1996 | Wenzhi | 436/161 |
| 5,589,069 A | * | 12/1996 | Wenzhi | 210/635 |
| 5,633,290 A | * | 5/1997 | Frechet | 521/54 |
| 5,807,687 A | * | 9/1998 | Jackman et al. | 435/7.1 |

FOREIGN PATENT DOCUMENTS

| | | |
|---|---|---|
| DE | 44 29 558 | 8/1994 |
| EP | 0 307 373 | 9/1988 |
| EP | 0 402 205 | 5/1990 |
| EP | 0 530 173 | 5/1992 |
| EP | 0 667 352 | 1/1995 |
| WO | 93 21190 | 4/1993 |
| WO | 94 24554 | 8/1994 |

OTHER PUBLICATIONS

"Viral Validation of the Manufacturing Process of High Purity Albumin From Placentas", Brown F. (ed.): Virological Safety Aspects of Plasma Derivatives Dev. Bio Stand. Basel, Karger, 1993, vol. 81, pp. 237–244.

"Safety of Placental Blood Derivatives", Jan. 15, 1994, vol. 343, The Lancet.

Chemical abstracts, vol. 121, No. 12, Sep. 26, 1994, Columbus, Ohio, US; Abstract No. 155840q, K. IIDA et al, A new, validated method for the destruction of conventional viruses and unconventional infectious agents, (e.g. BSE and scrapie) in proteins and sera), p. 884, column 1, XP002020258, see abstract , & Anim. Cell. Technol.: Basic Appl. Aspects, 1992, pp. 295–300.

Development in Biological Standardization, vol. 88, 1996, Basel CH, pp. 257–264, XP000197507, R. W. Kozak et al, "Transmissible spongiform encephalopathies (TSE): minimizing the risk of transmission by biological/pharmaceutical products: an industry perspective".

* cited by examiner

*Primary Examiner*—Maureen M. Wallenhorst
(74) *Attorney, Agent, or Firm*—Burns, Doane, Swecker & Mathis, L.L.P.

(57) ABSTRACT

The present invention is drawn to method for removing unconventional transmissible agents (UCTA) from aqueous protein solution. This method involves treating the aqueous protein solution with simultaneous electrostatic adsorption and hydrophobic chromatography. The method of the present invention is particularly suitable for treating calf serum or an albumin solution.

12 Claims, No Drawings

METHOD FOR REMOVING UNCONVENTIONAL TRANSMISSIBLE AGENTS FROM A PROTEIN SOLUTION

The invention relates to the sphere of removing unconventional transmissible agents (UCTA). More specifically, the invention relates to a process for removing UCTA from a protein solution.

The unconventional transmissible agents (UCTA), which include prions, are at the root of the subacute transmissible spongiform encephalopathies, which are slow degenerative diseases of the central nervous system whose development is always fatal; the agents which are responsible for these diseases have still not been identified.

These subacute transmissible spongiform encephalopathies affect both man and animals: → in man: kuru, Creutzfelt-Jakob disease, Gerstmann-Sträussler-Scheinker syndrome, fatal familial insomnia and, for certain people, Alpers disease. → in animals: natural sheep scrapie, transmissible mink encephalopathy, chronic wasting syndrome of wild ruminants in captivity and in the wild, and bovine spongiform encephalopathy.

The problem of removing UCTA from products of biological origin poses very great difficulties and is currently very poorly resolved, apart from a few exceptions.

The methods of inactivation which have been identified to date, such as treating with soda or Javelle water, or heating to temperatures higher than 130° C., cannot be applied to most biological substances, which are too fragile to withstand such physicochemical conditions.

While separation methods aimed at removing UCTA can in theory be the same as those which are used for proteins in general, i.e. filtration, selective adsorption, chromatography and ultracentrifugation, they meet with a very great difficulty. These methods are not nowadays used for removing traditional viruses since part of the infectivity always remains, even if this part is only a minimum but still sufficient to transmit the disease after the product has been injected. The inactivation methods are rightly preferred to them. The transmissible character of prions is as powerful as that of most viruses, and no chromatographic methods are currently available which are known to remove, with certainty, the last traces which may contaminate a complex protein solution. Filtration methods have been suggested for this purpose and have demonstrated their efficacy in clearing solutions of proteins of a molecular weight of less than 100 kilodaltons. Beyond that, these screening methods come up against the following difficulty: the size of the pores selected for stopping prions also stops large proteins, either because the protein has a mean hydrated diameter which is greater than that of the pore or because adsorption phenomena complicate filtration of the protein. These problems are met with, in particular, in the purification of animal sera which are used in cell culture methods for the purpose of preparing vaccines or drugs.

Similarly, when albumin is extracted from a biological material, whether human or animal, and when this albumin is intended for a therapeutic use, it is essential to treat the albumin in order to remove from it the unconventional transmissible agents which might possibly be present.

A process for purifying albumin from human placentas which affords all the guarantees of safety with regard to possible viral contamination is known from the article "Viral validation of the manufacturing process of high purity albumin from placentas", which was published in Brown F. (ed.): Virological Safety Aspects of Plasma Derivatives Dev. Bio Stand. Basel, Karger, 1993, vol. 81, pp. 237–244. As was mentioned in the article entitled "Safety of placental blood derivatives", which was published on Jan. 15 1994 in Vol. 343 of The Lancet, this process has been regarded as being particularly suitable for removing prions. This is because the purification steps carried out in this process include, in particular, three steps, i.e. FC1, FC2 and Hcol, of precipitation with alcohol in acid medium, combined with filtrations. Since prions have a tendency to coprecipitate with denatured proteins, these three steps, which involve the removal of substantial quantities of protein precipitates, are particularly appropriate for removing prions.

However, even if it is well suited for purifying placental albumin, this process is in no way appropriate for purifying all protein solutions, particularly not solutions of albumin of plasma origin. For example, the precipitation step FC1 is a step whose implementation conditions are such that haemoglobin is itself denatured and precipitated specifically; the quantity of haemoglobin is very low in plasma; this step would not therefore have the same characteristics, and albumin itself, in particular, would be exposed to denaturation by the chemical agent.

It is therefore desirable to have available a process for removing unconventional transmissible agents from a protein solution without altering the properties of the proteins which are present in the solution in any noteworthy manner.

The object of the invention is to propose such a process which is suitable for treating an aqueous protein solution, whether the solution be purified or not, in particular an albumin solution, an animal serum which is intended to be used for carrying out cell culture, a preparation of immunoglobulins of serum origin, or a preparation of factors which are involved in coagulation.

Another object of the invention is to propose a process which is capable of being employed industrially.

In order to achieve these objects, the present invention relates to a process for removing unconventional transmissible agents from an aqueous protein solution, characterized in that the process essentially consists in treating the protein solution by simultaneous electrostatic and hydrophobic adsorption chromatography and collecting the filtrate.

According to one embodiment of the invention, the protein solution is treated by electrostatic and hydrophobic chromatography in two steps, with one step being carried out at acid pH and the other step being carried out at approximately neutral pH.

According to one particular embodiment, the step at acid pH is carried out before the step at approximately neutral pH.

According to another embodiment of the invention, the protein solution is additionally treated by anion exchange chromatography.

According to another embodiment, the process of the invention additionally consists in carrying out a preliminary filtration of the protein solution using a filter whose cut-off threshold is approximately equal to 0.2 µm. In this way, the chromatography columns are protected from any blockage or bacterial contamination.

The present invention will be better understood from reading the detailed description which will now follow.

The protein solution from which any UCTA which may be present should be removed may have a variety of origins. It may be an unpurified protein solution which can be contaminated with prions or a purified solution, which may or may not originate from serum, such as preparations of immunoglobulins of serum origin and preparations which contain coagulation factors. Specifically, the protein solution may be an albumin solution of plasma origin which is obtained by a method which includes the Cohn fractionation technique. In all instances, the protein solution to be treated is an aqueous solution.

The gel which is used for carrying out the electrostatic and hydrophobic adsorption chromatography according to the invention is a macroporous gel which possesses functional groups, such as cross-linked products of diethylaminopolystyrene or diethylaminopolyphenyl, or any other combination of positive charge-carrying radicals and hydrophobic molecules linked to an inert matrix (for example silica, cellulose, sepharose or acrylamide). DEA-Spherosil/LS®, which is supplied by BIOSEPRA (USA, the address of whose office in France is 35 avenue Jean Jaurés-92390 VILLENEUVE LA GARENNE), is preferably used.

The column support may be equilibrated with standard buffers, for example sodium phosphate buffers, to which sodium chloride is preferably added.

In the specific case in which this chromatography is carried out in 2 steps, it is possible to use the same support for each of the steps with only the pH being changed.

According to one particular embodiment of the process according to the invention, the protein solution is additionally treated by anion exchange chromatography, in particular by passing it through a column which is loaded with diethylaminoethyl groups which are grafted onto an inert matrix (for example dextran-silica, cellulose, sepharose or acrylamide); use is made, for example, of a column of DEAE-Spherodex/LS®, which is supplied by BIOSEPRA (already identified above) and which is previously equilibrated with a buffer such that the surface electric charge is positive. A monosodium phosphate buffer of pH 6.8 may be used, for example.

Depending on the nature and expected use of the protein solution which is treated, it is furthermore possible to add, for safety, a supplementary step of non-specific adsorption chromatography, for example using a silica column, to the process according to the invention. This can be used to remove the components which may possibly have been released during the preceding steps.

According to one particular embodiment of the process of the invention, it is possible, after each treatment, to wash the chromatography columns with, for example, HCl solutions or an ethanol/HCl mixture, as well as carrying out a special wash with an NaOH solution at an arbitrarily chosen frequency, for example every 5 cycles.

When the columns have been washed, they can be stored, for example in a 70% solution of ethanol.

The fact of being able to use the same columns several times makes it possible to implement the process of the invention at the industrial level.

Surprisingly, it was observed that it was possible to use the process of the invention to separate UCTA from an aqueous solution of proteins, in particular albumin, even though the proteins and, in particular, the albumin have, like the UCTA, a tendency to become adsorbed on a hydrophobic support.

The following examples illustrate a few embodiments of the invention, in a non-restricting manner.

EXAMPLE 1
Preparation of a Contaminated Sample of Animal Serum

A contaminated sample of animal serum (calf serum in the examples selected, but this is applicable in the same way to other species or to other protein solutions) has to be prepared in order to demonstrate the qualities of the process of the invention. The prion source employed is a brain homogenate prepared from male C 57 BL/6 mice which had been infected with the experimental mouse scrapie agent (strain C 506/M3 in the 7th passage, which was supplied by Doctors D. C. Gajdusek and P. Prown of the NIH at Bethesda, USA, and whose infectious titre is approximately $10^8$ LD50 per gram of brain) and which have arrived at the terminal stage of the disease: 1 ml of brain homogenate is sonicated and mixed with 20 ml of serum.

EXAMPLE 2
First Method of Treating the Sample of Contaminated Calf Serum

A DEA-Spherosil/LS® column is prepared which contains 50 ml of support and which is equilibrated with a 0.02 M sodium phosphate buffer, pH 6.8, to which NaCl is added to the extent of 2 g/l. 10 ml of calf serum, which is supplemented with NaCl (2 g/l of serum) and contaminated with the scrapie strain as described in Example 1, are adjusted to pH 6.8, filtered through a 0.2 μm membrane and injected onto the chromatography column. The flow rate is adjusted to 100 ml/h for a column section equal to 5 $cm^2$, that is to a linear velocity of 20 cm/h. The filtrate which corresponds to the UV adsorption peak at 280 nm is collected and filtered under sterile conditions through a membrane of 0.2 μm porosity; samples are removed and stored at –70° C. for biological controls.

After treatment, the column is washed by passing through it five volumes of the following solutions:
1/0.1 N HCl
2/70% ethanol—0.1 N HCl
3/0.1 N NaOH The column is stored in 70% ethanol.

EXAMPLE 3
Second Method of Treating the Sample of Contaminated Calf Serum

In this case, a DEAE-Spherodex/LS® column, which contains 50 ml of support and which is also equilibrated with a 0.02 M sodium phosphate buffer, pH 6.8, which is supplemented with NaCl to obtain a concentration of 2 g/l, is prepared in addition.

This column is placed in series in front of the DEA-Spherosil/LS® column of Example 2.

The solution to be treated is the same as for Example 2.

The same conditions are used as for Example 2 except for the fact that the solution is treated consecutively by anion exchange chromatography, using the DEAE-Spherodex/LS® column, and then by electrostatic and hydrophobic adsorption chromatography using the DEA-Spherosil/LS® column.

The samples which are removed are also stored at –70° C. for biological controls.

EXAMPLE 4
Checking that the Column is not Contaminated

After a first cycle of purification in accordance with Example 2 or in accordance with Example 3, and after storing the columns in 70% ethanol for 15 h, a new cycle of purification is carried out using 10 ml of uncontaminated calf serum. The filtrate is also harvested and samples are removed for biological titration. These samples are analysed to demonstrate the absence of transmissible prion particles which might come from the previous purification cycle.

EXAMPLE 5
Third Method of Treating the Sample of Contaminated Calf Serum

The same experiment as that described in Example 3 is carried out at pH 5.0 instead of 6.8.

The two columns of DEAE-Spherodex/LS® and DEA-Spherosil/LS®, respectively, are equilibrated with a 0.02 M sodium phosphate buffer, pH 5.0, to which NaCl is added to the extent of 2 g/l. The serum is supplemented with 2 g of NaCl/1, also adjusted to pH 5.0 by adding HCl and filtered through a membrane of 0.2 μm porosity. The sequence of the experiment is identical to that in Example 3. At the end of the purification, the harvested serum is adjusted to neutral pH, by adding 1N NaOH, before being sampled and stored for biological controls.

EXAMPLE 6
Fourth Method of Treating the Sample of Contaminated Calf Serum

In this case, the serum is firstly passed through DEAE-Spherodex/LS® and then subsequently passed through DEA-Spherosil/LS®.

The serum is passed through the DEAE-Spherodex/LS® at pH 6.8, following 0.2 μm filtration, in accordance with the conditions described in Example 3 (without the DEA-Spherosil/LS® column).

The harvested fraction is then adjusted to pH 5.0 and injected onto the DEA-Spherosil/LS® column under the conditions described in Example 5 (without the DEAE-Spherodex/LS® column).

At the end of the purification, the harvested serum is adjusted to neutral pH, by adding 1N NaOH, before being sampled and stored for biological controls.

EXAMPLE 7
Fifth Method of Treating the Sample of Contaminated Calf Serum

This example is a variant of Example 6 in which the conditions under which the serum is passed through the first column of DEAE-Spherodex/LS® are different.

The contaminated serum is dialysed against 0.02 M sodium phosphate buffer, pH 6.8 (without any addition of NaCl). The same quantity of serum which has thus been treated is filtered through a membrane of 0.2 μm porosity and injected onto an identical column of DEAE-Spherodex/LS® which is equilibrated with 0.02 M sodium phosphate, pH 6.8 (without any addition of NaCl).

Under these conditions, a substantial part of the protein binds to the support while another part does not bind and is harvested in a first fraction (filtrate).

The bound fraction is eluted by injecting buffer to which NaCl is added to the extent of 10 g/l. The second fraction, corresponding to the eluate, is harvested. The whole of the two fractions (filtrate and eluate) is mixed, then filtered through a membrane of 0.2 μm porosity and applied to the DEA-Spherosil/LS® column, which is equilibrated at pH 6.8, as in Example 2.

The final harvested filtrate is sampled and stored for biological controls.

EXAMPLE 8
Sixth Method of Treating the Sample of Contaminated Calf Serum

This example resembles Example 7 except that the mixture which is collected from the outflow of the DEAE-Spherodex/LS® column is adjusted to pH 5.0 and the chromatography through the second column of DEAE-Spherosil/LS® [sic] is carried out in 0.02 M phosphate buffer, pH 5.0, to which NaCl is added to the extent of 5 g/l.

EXAMPLE 9
Biological Checks on the Samples of Treated Calf Serum

The samples which were removed at the end of each of the treatments carried out as described in Examples 2 to 8, and stored at −70° C., are checked using standard biological tests which are carried out on mice and which show that: the animal serum which has thus been treated no longer contains any components which are able to transmit scrapie to mice, the animal serum which has thus been treated retains its properties of stimulating cell multiplication and can be used in place of the animal serum which is currently available.

EXAMPLE 10

Treatment of a First Solution of Albumin 150 ml of a solution of albumin of placental origin which has been partially purified in accordance with the 4 precipitation steps and the dilution step described on p. 239 of the abovementioned article "Viral Validation of the Manufacturing Process of High Purity Albumin From Placentas" are available.

This solution is a 50 g/l solution of albumin in water and ethanol.

This solution is deliberately contaminated with 2% (v/v) of an inoculum containing UCTA. This inoculum is obtained by homogenizing the brains of animals (male C57BL/6 mice) which had been infected with the experimental mouse scrapie agent (strain C 506/M3 in the 7th passage, which was supplied by Drs. D. C. Gajdusek and P. Brown, N. I. H. Bethesda USA and whose infectious titre is approximately $10^8$ LD50 per gram of brain) and which have arrived at the terminal stage of the disease. The homogenate is prepared in a sterile 5% solution of glucose in accordance with a weight/volume ratio of 10%. The inoculum is sonicated and then clarified by centrifugation and filtered through a 0.45 μm filter before being used.

The contaminated albumin solution is filtered through a 0.2 μm filter and then treated consecutively by DEAE-Spherodex/LS® chromatography, then DEA-Spherosil/LS® chromatography at pH 4.8 and, finally, DEA-Spherosil/LS® chromatography at pH 6.8.

The first, or DEAE-Spherodex/LS®, column containing 30 g of gel is first of all equilibrated with monosodium phosphate buffer at pH 6.8.

The albumin solution is then injected into the column. The albumin, which is negatively charged, binds progressively to the support by ionic interaction. The alcohol and the protein impurities, which are electrically neutral or which are charged positively, are removed directly. The column is then rinsed with a 12.5% solution of alcohol and then with purified water. The albumin is subsequently eluted from the column by passing through a 10 g/l solution of NaCl. The column is then regenerated using a 60 g/l solution of NaCl, after which it is sterilized by an acid regeneration phase by means of washing with 0.1 N HCl; the column is then rinsed in a 70% solution of alcohol and stored in this solution.

The saline solution of albumin which is obtained is then subjected to chromatography on a DEA-Spherosil/LS® column containing 15 g of gel at pH 4.8. This chromatography combines electrostatic adsorption, due to the diethylamino groups, and hydrophobic adsorption, due to the crosslinked polystyrene products. The column support is previously equilibrated with a 0.7 g/l solution of NaCl. When the albumin solution is passed through this column, some hydrophobic impurities become bound while the albumin remains in solution. The column is then rinsed by passing through a 4 g/l solution of NaCl. The column is subsequently regenerated by washing with 0.1 N HCl, then washed with a 70% solution of alcohol and stored in the alcohol. The solution of albumin obtained from the outflow of this column is then subjected to a new step of chromatography on an identical support but in this case at pH 6.8. In this case, the column contains 3 g of gel and is combined with a column containing 3 g of silica. This step makes it possible to adsorb the hydrophobic impurities which are not bound at the pH at which the preceding step is carried out; it also makes it possible to any DEAE-dextran molecules which might come from the 1st chromatography. The 2 columns are then subjected to a first rinsing with a 6 g/l solution of NaCl in order to recover any albumin which may have been retained. The columns are then subjected to a second rinsing with a concentrated, 60 g/l solution of NaCl in order to remove any traces of denatured albumin. The columns are then regenerated by washing them with 0.1 N HCl, after which they are sterilized by being washed with a 70% solution of alcohol, and are then stored in the alcohol. 7.6 ml of a concentrated solution of pure albumin are then obtained from the outflow of the silica column.

In order to check for the presence of UCTA, a test is carried out on approximately 200 healthy male C 57BL/6 mice of 18–20 grams in weight, each of which is inoculated with 20 μl of albumin solution by the intracerebral route into the right hemisphere. The first 24 mice are given the concentrated albumin solution. The albumin solution is then diluted in 10-fold steps before being injected, with each of the dilutions being injected into 12 mice.

The animals are kept under observation in order to check for signs of the appearance of experimental mouse scrapie. A mouse is regarded as being positive after the second positive assessment of a clinical sign. When a mouse dies, its brain is frozen at −80° C. and a histopathological examination is carried out in order to confirm the cause of death. The results obtained demonstrate that the process of the invention results in a reduction in the infectious titre of the starting solution of albumin, as expressed in LD50 (which is determined by the method of Reed and Muench for dilutions of the tested sample carried out in 10-fold steps), of $10^{5.5}$, that is in a difference in titre of 5.5 log.

EXAMPLE 11

Checking that the Columns are not Contaminated

After having carried out Example 10, 150 ml are available of a 50 g/l solution of albumin which is identical to that of Example 10 except for the deliberate contamination with an inoculum containing UCTA; this albumin solution is taken through the same chromatography steps as those described in Example 10 in order to check that the UCTA which were adsorbed by the chromatography columns in Example 10 are not released into the new albumin solution. 6.6 ml of purified solution are obtained on this occasion. The same test as in Example 10 is then carried out; that is intracerebral inoculation, into each animal, of 20 μl of the albumin solution which has thus been obtained, and also the albumin solution which has been diluted in 10-fold steps. Approximately 100 mice are inoculated in this way. The results which are obtained demonstrate that the mice are not contaminated; the albumin solution is thus completely free of UCTA. It is therefore possible to use the chromatography columns several times over.

EXAMPLE 12

Treating a Second Solution of Albumin

The same experiment is carried out as in Example 10, but starting this time with an albumin solution which consists of the fraction V prepared by the cohn technique and which has been filtered through a 0.45 μm filter. The albumin solution which is then obtained exhibits the same characteristics as that obtained in Example 10.

What is claimed is:

1. A process for removing unconventional transmissible agents (UCTA) from an aqueous protein solution, wherein said process consists essentially of:

a) treating the protein solution by simultaneous electrostatic and hydrophobic adsorption chromatography; and b) collecting UCTA free filtrate from step a).

2. The process according to claim 1, wherein the simultaneous electrostatic and hydrophobic adsorption chromatography is carried out in two steps, with one step being carried out at acid pH and the other step being carried out at approximately neutral pH.

3. The process according to claim 2, wherein the step at acid pH is carried out before the step at approximately neutral pH.

4. The process according to claim 1, wherein the electrostatic and hydrophobic adsorption chromatography is carried out using a gel which possesses functional groups.

5. The process of claim 4, wherein said functional groups are selected from the group consisting of crosslinked products of diethylaminopolystyrene or diethylaminopolyphenyl, and any other combination of positive charge-carrying radicals and hydrophobic molecules linked to an inert matrix.

6. The process according to claim 1, wherein the electrostatic and hydrophobic adsorption chromatography is carried out using a macroporous support which possesses diethyl-amino groups.

7. The process according to claim 1, wherein the aqueous protein solution is a solution comprising albumin.

8. The process according to claim 1, wherein the aqueous protein solution is a solution comprising calf serum.

9. The process according to claim 1, wherein the aqueous protein solution is a solution comprising plasma proteins.

10. A process for removing unconventional transmissible agents (UCTA) from an aqueous protein solution, wherein said process consists essentially of:

a) treating the protein solution by simultaneous electrostatic and hydrophobic adsorption chromatography;

b) treating the aqueous protein solution by anion exchange chromatography; and c) collecting UCTA free filtrate from step b).

11. A process for removing unconventional transmissible agents (UCTA) from an aqueous protein solution, wherein said process consists essentially of:

a) treating the aqueous protein solution by anion exchange chromatography;

b) treating the protein solution by simultaneous electrostatic and hydrophobic adsorption chromatography; and c) collecting UCTA free filtrate from step b).

12. A process for removing unconventional transmissible agents (UCTA) from an aqueous protein solution, wherein said process consists essentially of:

a) carrying out a preliminary filtration of the protein solution using a filter whose cut-off threshold is approximately equal to 0.2 μm;

b) treating the protein solution by simultaneous electrostatic and hydrophobic adsorption chromatography; and c) collecting UCTA free filtrate from step b).

* * * * *